United States Patent
Goswami et al.

(10) Patent No.: US 6,753,021 B2
(45) Date of Patent: Jun. 22, 2004

(54) BIOLOGICALLY ACTIVE CHLOROFORM FRACTION OF AN EXTRACT OBTAINED FROM A MANGROVE PLANT SALVADORA PERSICA L

(75) Inventors: Usha Goswami, Goa (IN); Nazarine Fernandes, Goa (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/180,062

(22) Filed: Jun. 27, 2002

(65) Prior Publication Data

US 2002/0172731 A1 Nov. 21, 2002

Related U.S. Application Data

(63) Continuation of application No. 09/818,691, filed on Mar. 28, 2001, now abandoned.

(51) Int. Cl.$^7$ ............................................. A61K 35/78
(52) U.S. Cl. ..................... 424/765; 424/769; 514/906; 514/826
(58) Field of Search ............................. 424/725, 769; 514/906, 826

(56) References Cited

U.S. PATENT DOCUMENTS

| | | | |
|---|---|---|---|
| 5,009,886 A | 4/1991 | Ahmad et al. | |
| 5,190,979 A | 3/1993 | Herman | |
| 5,607,741 A | 3/1997 | Zimmerman et al. | |
| 5,804,206 A | 9/1998 | D'Amelio et al. | |
| 5,804,575 A | 9/1998 | Pezzuto et al. | |
| 5,910,307 A | 6/1999 | Kwak et al. | |
| 5,948,460 A | 9/1999 | Kang et al. | |
| 5,962,527 A | 10/1999 | Pezzuto et al. | |
| 6,048,847 A | 4/2000 | Ramadoss et al. | |

OTHER PUBLICATIONS

Nazarine, F., et al., "Pharmacological Activities of Extracts of Some Marine Animals and Plants on Isolated Tissues of the Guinea–Pig", Indian Journal of Marine Sciences, 27, 499–501 (1998).
Pisha, E., et al., "Discovery of Betulinic Acid as a Selective Inhibitor of Human Melanoma that Functions by Induction of Apoptosis", Nature Medicine, 1, 10, 1046–1051 (1995).
Fujioka, T., et al., "Anti–Aids Agents, 11. Betulinic Acid and Platanic Acid as Anti–HIV Principles from Syzigium Claviflorum, and the Anti–HIV Activity of Structurally Related Triterpenoids", Journal of Natural Products, 57, 2, 243–247 (1994).
Devi, et al., Bot. Mat., 1997, vol. 40, Pt. 2, pp. 87–91.
Devi, et al,, Bot. Mat., 1997, vol. 40, No. 6, pp. 533–535.
Devi, et al., Adv. Biosci., 1998, vol. 17, No. 2, pp. 75–84.
Ghazanfar, S., Handbook of Arabian Medicinal Plants, 1994, CRC Press, pp. 190–192.

Primary Examiner—Christopher R. Tate
(74) Attorney, Agent, or Firm—Piper Rudnick LLP; Steven B. Kelber

(57) ABSTRACT

The invention discloses a process of extracting, fractionating and purifying bioactive molecules from an associated mangrove plant, methods of screening for pharmacological activities of crude extract, its fractions and purified compounds and use of the chloroform fraction of the crude extract as anti-spasmodic, anti-arrhythmic and anti-cholinergic agent.

8 Claims, 5 Drawing Sheets

(1 of 5 Drawing Sheet(s) Filed in Color)

β-AMYRIN

BETULIN

URSOLIC ACID

METHYL PALMITATE

LUPEOL

PHARMACOLOGICAL TESTING CUM FRACTIONATION CHART OF EXTRACT FROM *SALVADORA PERSICA* LINNEAUS. 1753.
(DETAILS OF AQUEOUS FRACTION SHOWING TOCOLYTIC ACTIVITY)

BIOLOGICALLY ACTIVE CHLOROFORM FRACTION OF AN EXTRACT OBTAINED FROM A MANGROVE PLANT *SALVADORA PERSICA* L

This application is a continuation of U.S. application Ser. No. 09/818,691 filed Mar. 28, 2001, now abandoned, the contents of which are incorporated herein by reference.

FIELD OF THE INVENTION

The invention relates to a biologically active chloroform fraction of extracts obtained from the plant *Salvadora persica* Linneaus 1753. The invention also relates to a process for obtaining the crude extract and obtaining the chloroform fraction. Further, the invention relates to pharmaceutical compositions exhibiting biological activity.

BACKGROUND OF THE INVENTION

The mangrove plant, *Salvadora persica* Linneaus, 1753, belongs to the order Salvadoracea. Mangrove plants are shrubs or small trees with white flowers frequently found in degraded mangrove swamps and saline banks all over the west coast of India. Large numbers of marine plants have been examined for bioactive substances. Nazarine et al. have reported promising pharmacological activities in marine organisms from Indian waters. (Indian Journal of Marine Sciences 27:499–501 (1998)).

There are several patents available from all over the world relating to processes and compounds obtained from natural sources for various purposes. Kwak et al. patented a process of extracting and purifying biologically effective ingredients from combined medicinal plants and their extract composition (U.S. Pat. No. 5,910,307 issued on Jun. 8, 1999). D'Amelio et al. disclosed a therapeutic composition and method for treating skin using an extract from the *Centipeda cunninghami* plant. (U.S. Pat. No. 5,804,206 issued on Sep. 8, 1998). Zimmerman et al. isolated a compound from the methanolic extract of the eelgrass *Zostrea marina* which has significant antifouling aquatic properties. (U.S. Pat. No. 5,607,741 issued on Mar. 4, 1997).

Betulinic acid, which is prepared from the compound betulin, has many pharmaceutical potentials. Pezzuto et al. disclosed methods of manufacturing betulinic acid from betulin (U.S. Pat. No. 5,804,575 issued on Sep. 8, 1998). Betulinic acid is intensively investigated as a potential therapeutic agent for a variety of diseases. (U.S. Pat. No. 5,962,527 issued to Pezzuto et al. on Oct. 5, 1999). Pisha et al. disclose that betulinic acid has selective antitumour activity against human melanoma, e.g., MEL-1, MEL-2 and MEL-4. (Nature Medicine, pp.1046–1051 (1995)). Fujioka et al. disclose that betulinic acid has anti-HIV activity in H9 lymphocytic cells. (*J. Nat. Prod.* 57(2) pages 243–247 (1994)). However, research directed to betulinic acid as a therapeutic agent are hindered because betulinic acid is available in very limited quantities and at a very high cost. Ramadoss et al. describe uses of betulinic acid and its derivatives for inhibiting cancer growth and a method of monitoring the growth. (U.S. Pat. No. 6,048,847, issued on Apr. 11, 2000). Kang et al. disclosed flavored product additives in which ursolic acid was one of the compounds in a group of three compounds which was added to a flavored product to reduce aftertaste in the product and enhance its sweetness. (U.S. Pat. No. 5,948,460 issued on Sep. 7, 1999). Ursolic acid was also used as a constituent in a preparation for inhibition of skin Tumorigenesis. Id. Herman disclosed that lupeol can make terpene ozonides (which have medicinal value) pharmacologically active. (U.S. Pat. No. 5,190,979 issued Mar. 2, 1993).

SUMMARY OF THE INVENTION

The main object of the present invention is to provide a process for obtaining the chloroform fraction from the crude extract from stems, leaves, and flowers of *Salvadora persica*.

A further object of the invention is to study the biological activity of the chloroform fraction from the crude extract from stems, leaves, and flowers of *Salvadora persica*.

Another object of the invention is to isolate naturally occurring compounds from the plant *Salvadora persica* and to identify their molecular weights, molecular formulas, melting points and their structural formulae.

Yet another object of the invention is to screen the chloroform fraction of the crude extract, its fractions, and purified compounds to ensure that the activities shown by the crude extract and chloroform fraction are maintained.

A further object of the invention is to provide pharmaceutical compositions that contain chloroform fractions of the extract from the plant *Salvadora persica* which exhibit biological activity.

It is yet another object of the invention to provide pharmaceutical compositions containing the extract obtained from the plant *Salvadora persica*.

The present invention seeks to overcome the drawbacks inherent in the prior art by providing a highly efficient and selective means for processing active crude extract as well as fractionation, isolation and purification of the active compounds.

DESCRIPTION OF THE FIGURES

The file of this patent contains at least one drawing executed in color. Copies of this patent with color drawings will be provided by the Patent and Trademark Office upon request and upon payment of the necessary fee.

FIG. 1(*b*) is an illustration of the twig of the mangrove plant used in the instant invention;

DETAILED DESCRIPTION OF THE INVENTION

Figure 1A:
FIG. 1(*a*) is an illustration of a mangrove plant.
Figure 1B:
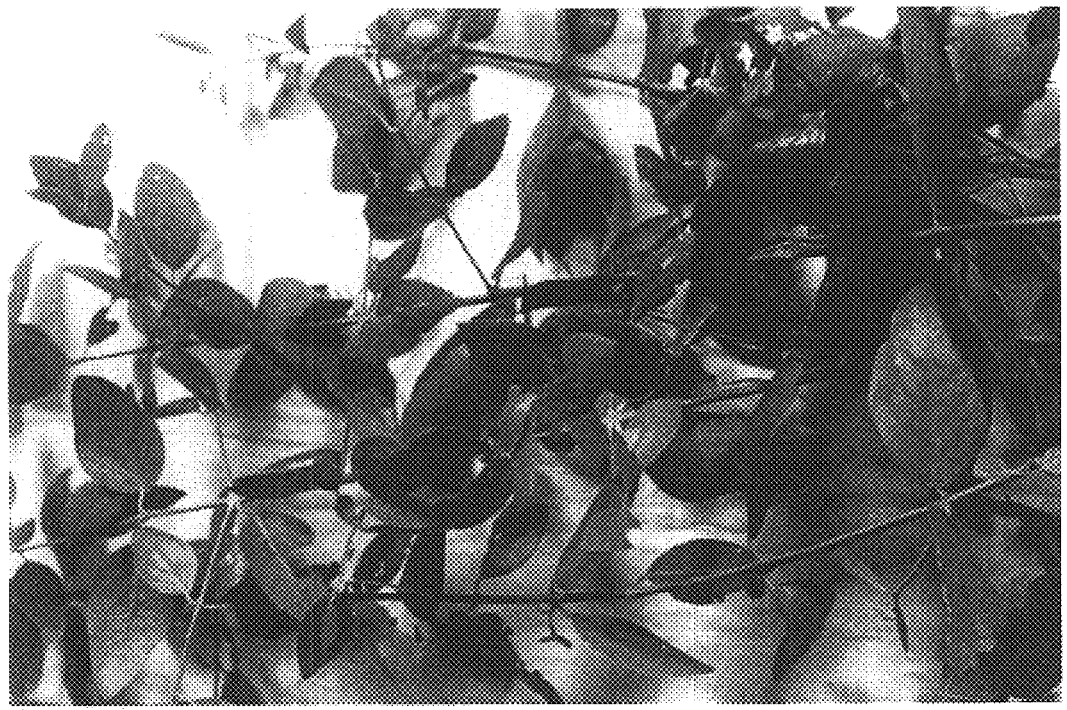

The present invention discloses methods of isolation, purification, and pharmacological screening of commercially important compounds from a commonly available plant from mangrove swamps of the west coast of India, namely the associated mangrove plant *Salvadora persica*. *Salvadora persica* is a shrub and the twigs with leaves of flowers can be hand picked. The crude extract and fractions from the plant exhibit therapeutic value. In particular, the biological activity shown by the extract is maintained in the purified compounds such as methyl palmitate and betulin.

This application discloses potential clinical uses of the extract and fractions for treatment of diseases such as bronchial asthma and renal colics. The extract and fraction also act as a smooth muscle relaxant and aids in the prevention of premature delivery. The application also relates to the use of methyl palmitate and betulin for treating motion sickness and abdominal cramps.

The invention provides methods of preparing biologically active crude extracts of an associated mangrove plant identified as *Salvadora persica* Linneaus 1753. *Salvadora persica* Linneaus (Salvadoraceae) are shrubs or small trees with white flowers frequent in degraded mangrove swamps and saline banks throughout the west coast of India and west Asia. The process disclosed further relates to the extraction, fractionation, and purification of active constituent metabolites of the said plant. In addition, the invention discloses the spectral identification of the compounds such as β-amyrin (non-steroidalpolycyclic triterpene), betulin, ursolic acid (triterpenic acid), methyl palmitate (aliphatic ester), and lupeol (non-steroidalpolycyclic triterpene). The invention also discloses with molecular formulas, molecular weights, melting points, and structural formulas of the compounds. The present invention provides highly efficient and selective methods for processing active crude extracts obtained from *Salvadora persica*, as well as fractionation, isolation, and purification of the extracts. As used herein, the term fractionation means separating the crude extract. The term isolation and fractionation mean separating the fraction into pure compounds.

The present invention further discloses methods of screening for pharmacological activities of the compounds in mammalian tissues. It has been discovered that the crude extract obtained from the plant *Salvadora persica* can be separated into two fractions, i.e., chloroform and aqueous fractions. The chloroform fraction exhibits antispasmodic, anti-cholinergic, and anti-arrhyth activities, which is described in detail herein.

The present invention has a novel approach for the pharmacological screening of anti-arrhythmic activity on atrial tissues. In particular, the left atrium was used for electric stimulations rather than the right atrium which has the pacemaker. This method was found to be advantageous for longer survival of the atrium during experiments.

Accordingly, the invention provides a process of extracting and purifying biologically useful and active molecules from an associated mangrove plant that includes the steps of:

i) collecting and processing the plant parts of *Salvadora persica*, ii) preparing a crude extract from the plant parts of *Salvadora persica*, iii) testing the crude extract using pharmacological methods, iv) fractionating the crude extract, v) testing the fractions using pharmacological methods, vi) isolating the pure compounds by column chromatography, vii) testing the pure compounds by using pharmacological methods, and viii) identifying the compounds by spectroscopy.

According to another embodiment of the present invention, the chloroform fraction of the mangrove plant *Salvadora persica* showed arrhythmic, anti-spasmodic, and anti-cholinergic activity as the parent crude extract.

The invention also provides the identification of the five molecules, structural formulae, and molecular formulae from spectral data. Additionally the invention obtains the molecular weights of the molecules from EIMS.

A crude extract was obtained from the plant *Salvadora persica* and was tested for bioactivity. If found promising in terms of its pharmacological activity, the extract was fractionated using solvents with increasing polarity to obtain fractions such as petroleum ether, chloroform, butanol, and aqueous fractions. Each of these fractions were also tested for their pharmacological activity.

The five compounds purified from the extract of the plant were β-amyrin (non-steroidalpolycyclic triterpene), betulin, ursolic acid (triterpenic acid), methyl palmitate (aliphatic ester), and lupeol (non-steroidalpolycyclic triterpene).

β-amyrin was determined to be a non-steroidalpolycyclic triterpene with the following details:

| Molecular formula: | $C_{30}H_{50}O$ |
|---|---|
| Molecular weight: | 426 |
| Melting point: | 160° C. |

Betulin was determined to have the following properties:

| Molecular formula: | $C_{30}H_{50}O_2$ |
|---|---|
| Molecular weight: | 442 |
| Melting point: | 255° C. |

Ursolic acid (triterpenic acid) was determined to have the following properties:

| Molecular formula: | $C_{30}H_{48}O_3$ |
|---|---|
| Molecular weight: | 456 |
| Melting point: | 292° C. |

Methyl palmitate (aliphatic ester) was determined to have the following properties:

| Molecular formula: | $C_{16}H_{32}O_2$ |
|---|---|
| Molecular weight: | 256 |
| Melting point: | 30° C. |

Lupeol (non-steroidalpolycyclic triterpene) found in the extract was determined to have the following properties:

| Molecular formula: | $C_{30}H_{50}O$ |
|---|---|
| Molecular weight: | 426 |
| Melting point: | 215° C. |

Betulin can be used in manufacturing of betulinic acid (U.S. Pat. No. 5,804,575 issued on Sep. 8, 1998). Betulinic acid is being intensively investigated as a potential therapeutic agent for a variety of diseases.

Ursolic acid is added to a flavored product to reduce the aftertaste in the product and to enhance its sweetness, such as, for example, in a diet drink. It is also used as a constituent in a preparation for the inhibition of skin Tumorigenesis.

Extracts of some plants which show vasoconstrictor and analgesic properties also contain triterpenoid β-amyrin. Compositions for inhibiting the formation of unwanted skin pigmentation combine high tyrosinase blocking capabilities with stability in cosmetic preparations, absence of significant cytotoxic effects and synergy of action (See U.S. Pat. Nos. 5,773,014 and 5,679,393). β-amyrin and lupeol are used as components for dimethylsterols in medical formulations. (See U.S. Patent No. 4,808,574).

Methyl palmitate is a compound used in making alcohols as mentioned in U.S. Pat. No. 6,049,013 issued in April, 2000. Lupeol can be used as a component for several remedial medicines, as insect repellents, in distilleries, as an anti-tumor agent, and in the chemical industries. (See U.S. Pat. Nos. 4,808,574; 5,962,527; and 5,908,628).

Thus, it was determined that the extract of *Salvadora persica* contained several compounds as listed above. The chloroform fraction of the extract of the plant *Salvadora persica* was then tested for its biological activity on guinea pigs. It was surprisingly discovered that the extract exhibited excellent anti-cholinergic, anti-arrhythmic, and anti-spasmodic activity.

Accordingly, the present invention provides compositions containing the chloroform fraction of the extract obtained from *Salvadora persica*, optionally with conventional additives, for inhibition of treatment of anti-cholinergic conditions such as asthma. In a preferred embodiment, the composition may contain about 10 μgm of the extract. The chloroform fraction of the extract obtained from the plant *Salvadora persica* is a potential anti-cholinergic agent. The compositions may be formulated in different physical forms, as may be required. The extract may be used as such or with conventional additives, physiologically acceptable carriers, preservatives, buffers, etc., as required. Such would be easily determined by one of ordinary skill in the art.

Additionally, the invention provides a method of treating anti-cholinergic conditions such as bronchial asthma, which includes the administration of a therapeutically effective amount of the extract obtained from *Salvadora persica* to the subject in need thereof. The extract may be administered at a dosage level in the range of 50 μg/ml to 250 μg/ml, in case of normal adults. The exact dosage will vary depending on the patient to be treated and will depend on factors such as requirements of the patient, severity of the condition being treated, and the activity of the extract. The determination of optimum dosages for a particular patient is well-known to those skilled in the art.

Further, it was determined that the chloroform fraction of the extract obtained from the plant *Salvadora persica* exhibits anti-spasmodic activity. Accordingly, the present invention provides compositions containing the chloroform fraction of the extract obtained from *Salvadora persica*, optionally with conventional additives for the inhibition of treatment of spasmodic conditions such as muscular spasms. Thus, the chloroform fraction of the extract obtained from the plant *Salvadora persica* is a potential anti-spasmodic agent. In a preferred embodiment of the present invention, composition contains about 10 μgm of the extract. The compositions may be formulated in different physical forms, as may be required. The extract may be used as such or with conventional additives, physiologically acceptable carriers, preservatives, buffers, etc. as required, which would be readily identified by one skill in the art.

Additionally, the invention provides a method of treating spasmodic conditions such as bronchial asthma, which includes the administration of a therapeutically effective amount of the extract obtained from *Salvadora persica* to the subject in need thereof The extract may be administered at a dosage level in the range of 50 μg/ml to 250 μg/ml, in the case of normal adults. The exact dosage will vary depending on the patient to be treated, and will depend on factors such as the requirements of the patient, the severity of the condition being treated, and the activity of the extract. The determination of optimum dosages for a particular patient would be easily ascertained by those skilled in the art.

Furthermore, it has been discovered that the chloroform fraction of the extract obtained from the plant *Salvadora persica* exhibits anti-arrhythmic activity. Accordingly, the invention discloses compositions that contain the chloroform fraction of the extract obtained from *Salvadora persica*, optionally with conventional additives for the inhibition of treatment of arrhythmias of the heart. Thus, the chloroform fraction of the extract obtained from the plant *Salvadora persica* is a potential anti-arrhythmic agent. In a preferred embodiment, the composition contains about 10 μgm of the extract. Compositions may be formulated in different physical forms, as may be required. Further, the extract may be used as such or with conventional additives, physiologically acceptable carriers, preservatives, buffers, etc. as required. Any such additives would be easily identified by one of skill in the art.

Additionally, the invention provides a method of treating arrhythmias of the heart, which includes the administration of a therapeutically effective amount of the extract obtained from *Salvadora persica* to the subject in need thereof. In a preferred embodiment, the extract is administered at a dosage level in the range of 3 μg/ml to 10 μg/ml, in the case of normal adults. The extract is administered to the subject for a period of 10 minutes. The exact dosage will vary depending on the patient to be treated and will depend on factors such as the requirements of the patient, the severity of the condition being treated, and the activity of the extract. The determination of optimum dosages for a particular patient would be easily determined by one skilled in the art.

The invention is described in detail and illustrated by the following examples which should not be construed as limitations on the inventive concept embodied herein.

EXAMPLES

Example 1

Chemicals, Reagents, and Apparatus Used, and Their Sources

| Name of reagent/chemicals | Company |
| --- | --- |
| Aqueous methanol | Sisco Research Laboratories Pvt Ltd. |
| Petroleum ether | Ranbaxy Fine Chemicals Ltd. |
| Chloroform | Sisco Research Laboratories Pvt. Ltd. |
| Butanol | Sisco Research Laboratories Pvt. Ltd. |
| Ethyl acetate | Sisco Research Laboratories Pvt. Ltd. |
| Histamine acid phosphate | Blenkinsop & Co. Ltd. |
| Acetylcholine chloride | Hopkin & Williams Ltd. |
| 5-Hydroxytryptamine creatine sulphate | Sigma Chemicals |
| Barium chloride | Apex Chemicals |
| Nicotine sulphate | BDH Chemicals |
| Oxytocin | Parke Davis India Ltd. |
| Prostodin-PGF 2 alpha | Astra IDL Ltd. |

APPARATUS

1. Physiograph Company: Biodevices, Ambala, India
2. Force Transducer Model No. T-305 Company: GRASS, USA
3. Stimulator Model SS44 Company: Biodevices, Ambala, India
4. Polygraph Model 7 Company: GRASS, USA
5. Force Transducer Model No. FT-03 Company: GRASS, USA
6. Organ Bath Ambala, India

Example 2

Collection

Collection of the mangrove plant *Salvadora persica* L from the coast of Goa, a state in India, was along the Ribandar, near the mouth of the Mandovi estuary, upstream. This species is ubiquitous to the coastal areas of Goa and was collected manually from the intertidal banks.

Example 3

Processing of the Collected Mangrove Plants

The collected mangrove were washed first with seawater and then washed with tap water. The undesired materials were sifted out while washing with tap water to get rid of the salts. The leaves, stems, and flowers of the associated mangrove plant were air dried. After drying, the plant material was cut into small pieces and immersed in 90% aqueous methanol(solvent) for a week for extraction. Care was taken to ensure that these were properly soaked/dipped in the solvent and checked for putrefaction.

Example 4

Extraction and Preparation

Extraction and preparation of the crude extract was carried out by a cold percolation method at room temperature and by solvent evaporation at a water bath (temperature 50° C.) under reduced pressure. This helps to protect any heat labile metabolite present in it. Re-extraction was done twice until the extract was concentrated under vacuum to obtain the crude extract.

Example 5

Fractionation of the crude extract

The crude extract was partitioned into petroleum ether, chloroform, n-butanol, and aqueous fractions using a separating funnel. Petroleum ether was added to the extract in the separating funnel and separated out. Next, chloroform was added to the residue, mixed well, and the lower layer separated. To the residue, butanol was added. The top layer was the butanol fraction and lower layer was the aqueous fraction. Extraction of each fraction was done three times and, whenever there was emulsion, sodium chloride was added to break the emulsion. Sodium sulphate was added to the chloroform and butanol fractions to remove traces of water before concentration. All of the fractions were concentrated in the same manner as the crude extract. These fractions were tested for the same pharmacological activity as the parent crude extract. Column chromatography for isolation of pure compound was done by repeated column chromatography and thin layer chromatography (TLC) of the eluents. The TLC revealed compounds such as β-amyrin, betulin, ursolic acid, and lupeol.

Example 6

To obtain the compounds β-amyrin and betulin, separation by thin layer chromatography was carried out on 0.25 mm thick silica gel plates (Qualigen). The eluent was a 90:10 (v/v) petroleum ether/ethyl acetate mixture and the spots were developed by spraying with a 5% $H_2SO_4$ solution and fixation by heating at 110° C.

For the compounds ursolic acid and methyl palmitate, separation by thin layer chromatography was carried out on 0.25 mm thick silica gel plates (Qualigen). The eluent was a 85:15 (v/v) petroleum ether/ethyl acetate mixture and the spots were developed by spraying with a 5% $H_2SO_4$ solution and fixation by heating at 110° C.

For the compound lupeol, the separation by thin layer chromatography were carried out on 0.25 mm thick silica gel plates (Qualigen). The eluent was a 75:25 (v/v) petroleum ether/ethyl acetate mixture and the spots were developed by spraying with a 5% $H_2SO_4$ solution and fixation by heating at 110° C.

Figure 2:
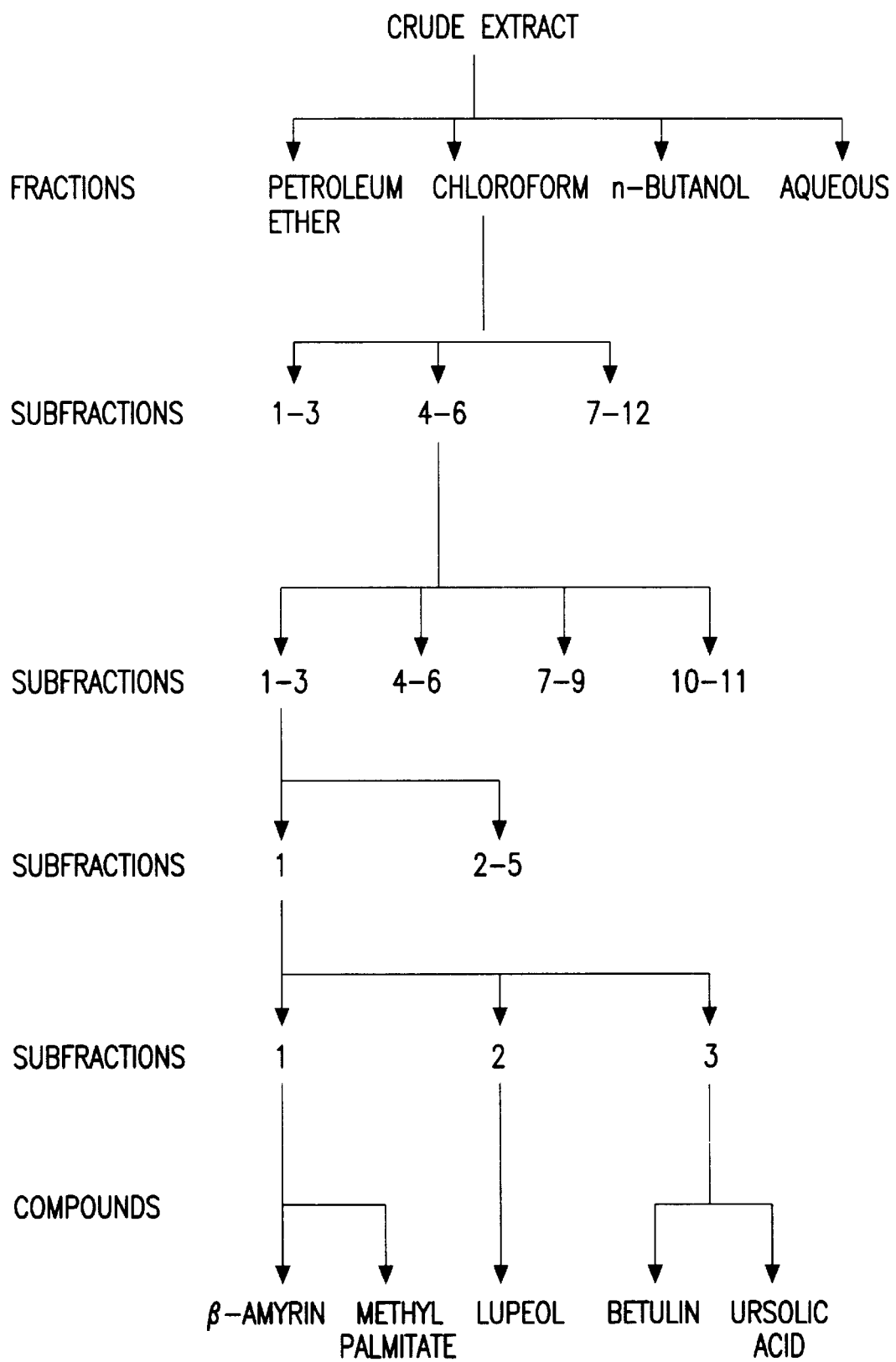
Figure 3:
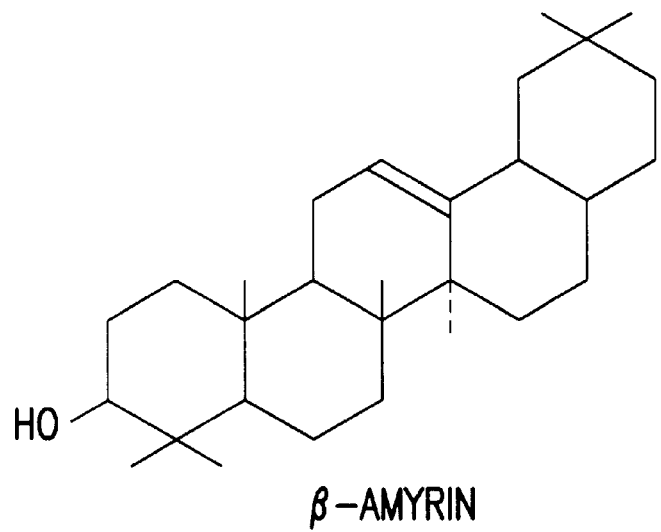
FIG. 3 is an illustration of the structural formula of β-amyrin (non-steroidalpolycyclic triterpene)
Figure 4:
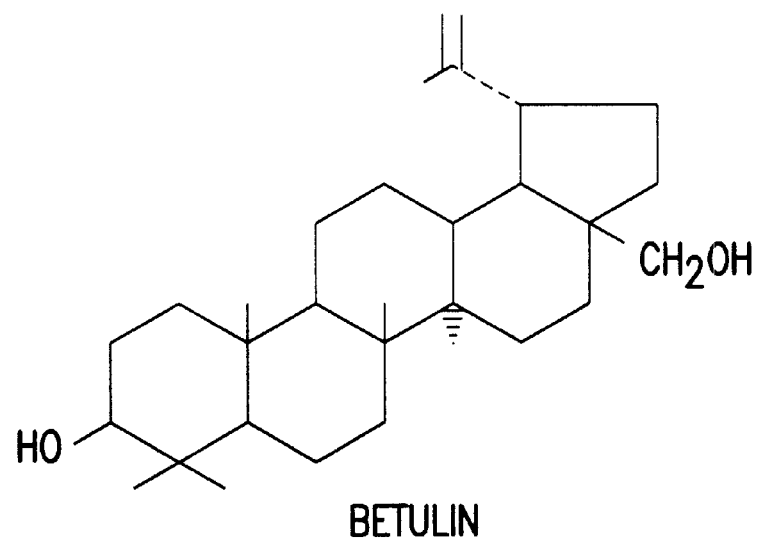
FIG. 4 is an illustration of the structural formula of Betulin.
Figure 5:
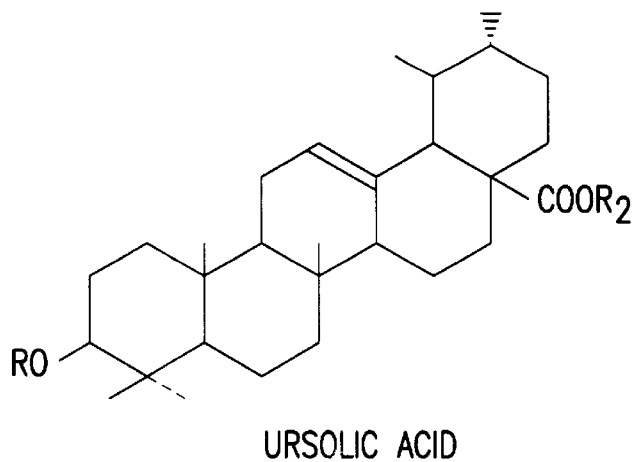
FIG. 5 is an illustration of the structural formula of Ursolic acid (triterpenic acid)
Figure 6:
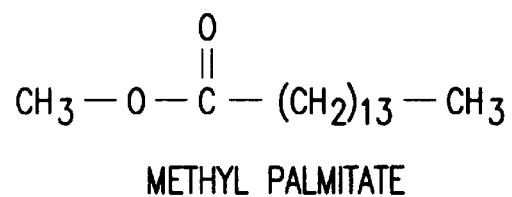
FIG. 6 is an illustration of the structural formula of methyl palmitate (Aliphatic ester)
Figure 7:
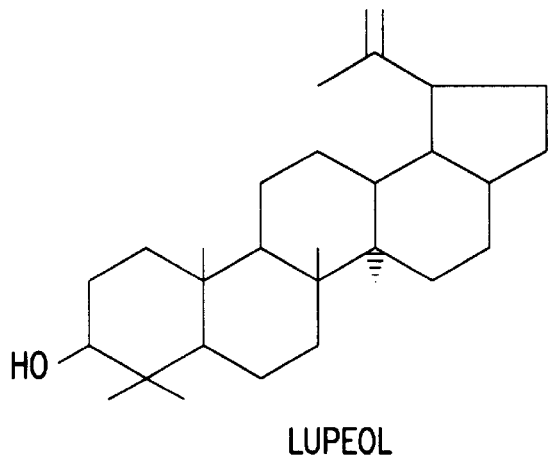
FIG. 7 is an illustration of the structural formula of Lupeol (non-steroidalpolycyclic triterpene)
Figure 8:
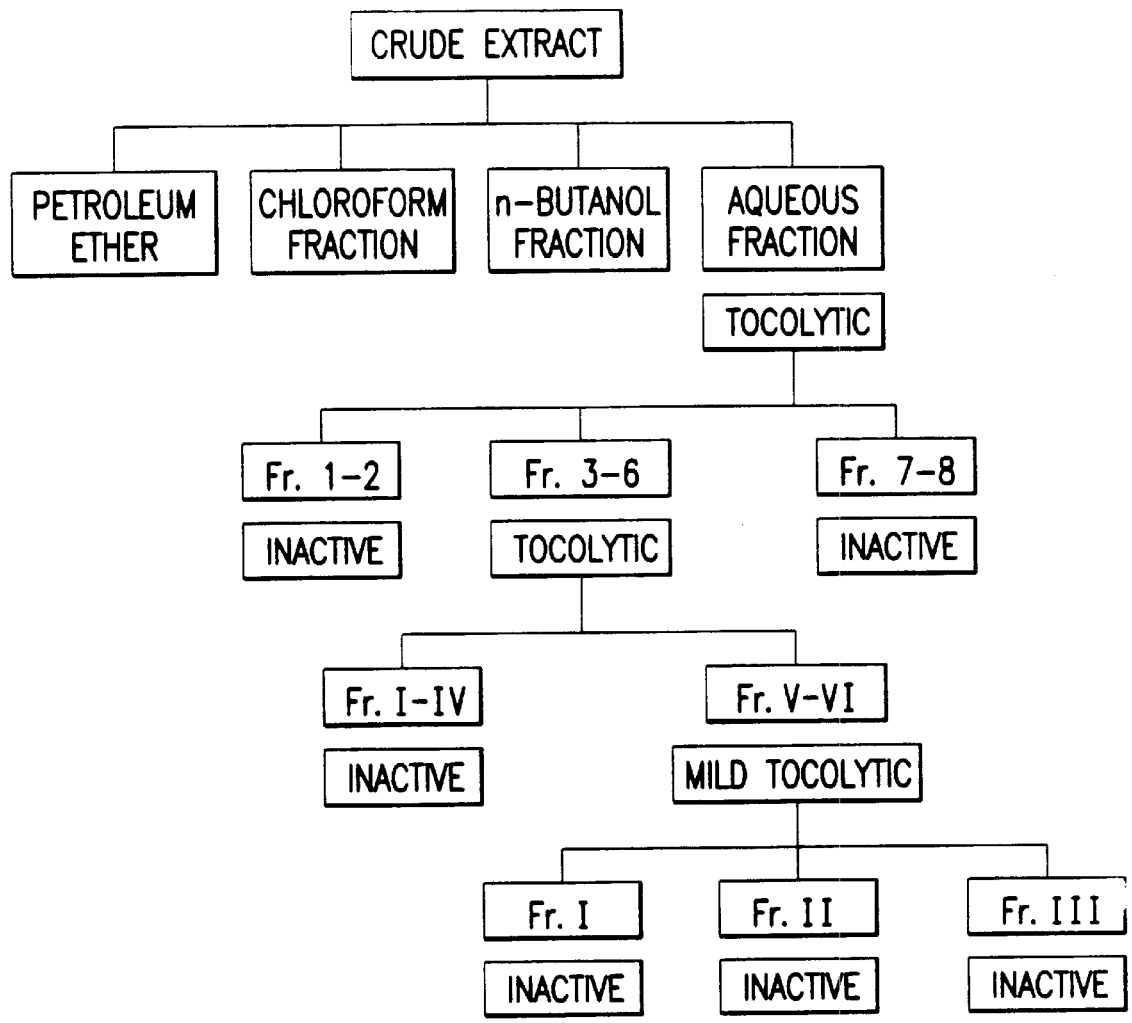
FIG. 8 is the fractionation chart of the extract of *Salvadora persica*

In the present invention, the active chloroform fraction of the mangrove plant *Salvadora persica* was column chromatographed over silica gel for the isolation of the active constituent. Elutes from the column with the same TLC profile were mixed and subjected to pharmacological testing. The active sub-fractions were further chromatographed until active pure compounds were obtained. (FIG. 2). Spots on the thin layer chromatography (TLC) were visualized using iodine vapors and spraying with methanolic sulphuric acid.

TLC was done on glass plates (20×20 cms) coated with a 0.25 mm layer of TLC grade silica gel (Qualigen) activated at 110° C. for 1 hour before use. The active aqueous fraction was passed through a XAD-column and the eluents were treated, as mentioned above, for the isolation and purification of active constituent metabolites.

The five compounds were identified on the basis of spectral data obtained at the Regional Sophisticated Instrumentation Center (RSIC) India by the following spectra:

$^1$HNMR for determining the proton environment of the molecule carried out on Bruker DPX-200 MHz.

| Apparatus: | Bruker Spectrometer |
| Model: | DPX |
| Company: | Bruker |

$^{13}$CNMR for carbon atoms Bruker DPV 300 MHz.

The compounds were identified from a comparison of their spectral data with those of similar compounds reported in literature.

Mass spectra: Electron impact mass spectrometry (EIMS) for determining the molecular weights, along with its fragmentation pattern, was carried out on a mass spectrometer (El/CIMS) Model D.300 JEOL.

| Apparatus: | Mass Spectrometer (EIMS) |
| Model: | D-300 |
| Company: | JEOL, Japan |

Example 7

Pharmacological Testing of Pure Compounds

The standard drugs used were as follows:

Histamine acid phosphate (Blenkinsop & Co. Ltd.) on ileum.

Acetylcholine chloride (Hopkin & Williams Ltd.) on ileum.

5-Hydroxytryptamine creatinine sulphate (Sigma Chemicals Co.) on gastrointestinal tract.

Barium chloride (Apex Chemicals) on smooth muscle contraction.

Nicotine sulphate (BDH Chemicals) on intestine as ganglion stimulant.

Tyrode was used on guinea pig ileum and Ringer-Locke physiological solution was used on guinea pig atria.

All other reagents used were of analytical grade.

Various parameters of the physiological solutions were as follows:

All physiological solutions were prepared fresh at the time of the experiment.

pH: The pH of the various physiological salt solutions varied between 7.3 and 7.4. At lower pH, the tonus of the preparation tended to decrease and was therefore liable to alter the effect of the drugs.

Temperature: In order to get consistent effects, it was important to maintain the temperature of the bath solution at a specified level. If the temperature was decreased below 37° C., the tonus of the intestine was increased, the contractions became smaller, and the contraction and relaxation times increased.

Air: Air or oxygen is needed for proper functioning of the tissues. Besides providing oxygen to the tissues, the stream of gas bubbles also stirred the bath solution, thereby facilitating the diffusion of the drugs added to the bath. The solution in the bath was changed frequently because prolonged aeration tended to alter the pH.

In vitro Experiments

Female, virgin guinea pigs weighing around 300 to 350 g, housed under uniform husbandry conditions (temperature 25±1° C.) were used. The animals were starved 24 hours prior to the experiment, only water was provided ad libitum.

The isolated guinea pig ileum was used to study the anti-spasmodic, anti-cholinergic, and anti-arrhythmic activity of the active fractions.

A. ANTI-CHOLINERGIC ACTIVITY

The active fractions were isolated for anti-cholinergic activity. In particular, the five compounds isolated were tested only on isolated guinea pig ileum. The longitudinal ileal muscle from a freshly killed guinea pig was suspended in an organ bath of 10 ml capacity, filled with Tyrode solution, and aerated with air. The Tyrode solution included the following components:

| | |
|---|---|
| Glucose | 1.0 g |
| Sodium chloride | 8.0 g |
| Sodium bicarbonate | 1.0 g |
| Potassium chloride | 0.2 g |
| Calcium chloride | 0.2 g |
| Magnesium chloride | 0.1 g |
| Sodium hydrogen phosphate | 0.05 g |

All of these compounds were dissolved in 1000 ml of distilled water.

Two to four doses of acetylcholine were added to the bath to obtain uniform amplitude with a contact period of 30 seconds, the contractions of which were recorded on a polygraph. The five compounds isolated were tested in doses of 196 and $392 \times 10^{-6}$ moles per ml of bath concentration. The effects of the compounds against acetylcholine—induced contraction was observed and the percentage reduction of contraction was measured.

B. ANTI-SPASMODIC ACTIVITY

The active fractions were isolated for anti-spasmodic activity. The compounds isolated were tested only on isolated guinea pig ileum. The longitudinal ileal muscle from a freshly killed guinea pig was suspended in an organ bath of 10 ml capacity, filled with Tyrode solution, and aerated with air.

For pharmacological testing on guinea pig ileum, the guinea pig was sacrificed by stunning with a sharp blow on its head. The abdomen was then quickly cut open. Towards the lower end of the abdomen was the greenish sac-like caecum. The small intestine was marked by a localized thickening in the wall—a Peyer's patch of lymphoid tissue. The lowermost 10 cm of ileum nearest to the ileocaecal-junction was discarded. From there, about 10 cm of ileal tissue was cut off and freed of mesentery and placed in a petridish containing warm Tyrode solution. The lumen of the ileum was gently rinsed using a hypodermic syringe filled with Tyrode solution to prevent accumulation of mucus in the lumen. The ileum was cut into small segments of about 3–4 cm in length in the fully relaxed state. The lower end was sutured to a tissue holder by making a loop first to avoid direct contact with the tube. The tissue was positioned in an organ bath with a capacity of 10 ml containing Tyrode solution and was aerated with air at 37° C. The thread of the upper end of the ileum was fixed to the lever of a force transducer (FT 03) which measured the muscle contractions isometrically. The force transducer was connected to a Grass Polygraph (Model 7) which recorded the muscle contractions. The ileal tissue was kept to stabilize in the Tyrode solution for 30 minutes. The fluid in the organ bath was renewed every 10 mins (as the pH changed).

Two to four does of the standard drug spasmogens (acetylcholine, histamine, 5-hydroxytryptamine, barium chloride, and nicotine) were added to the bath to obtain uniform amplitude with a contact period of 60 seconds, the contractions of which were recorded on a polygraph. The chloroform extract was added one minute before the addition of the spasmogens. The effect of the compounds against acetylcholine—induced contraction was observed and the percentage reduction of contraction was measured.

C. ANTI-ARRYTHMIC ACTIVITY

In vitro experiments were performed on isolated guinea pig atria.

The thorax of the stunned guinea pig was quickly opened by cutting the sternocostal junctions. The heart was seen behind the sternum, beating in its pericardial covering. It was nicked off and placed in a petridish containing Ringer-Locke solution aerated with pure oxygen. It was gently squeezed to remove blood from the cavities of the atria and the ventricles and to prevent clotting of blood inside the coronary arteries. All other tissues were cut away until nothing was left except the auricles, which appeared as a pair of rapidly beating pale pink leafy structures. Threads were tied to the tip of each auricle. The right atrium having the pacemaker was tied to the glass oxygen tube and mounted in an organ bath of capacity 40 ml containing Ringer-Locke solution at 34° C. and oxygenated. The thread at the other end of the left auricle was fixed to the transducer (Force transducer T-305) which was connected to a Biodevices Physiograph. The composition of the Ringer-Locke solution was as follows:

| | |
|---|---|
| Glucose | 0.5 g |
| Sodium chloride | 9.0 g |
| Sodium bicarbonate | 0.5 g |
| Potassium chloride | 0.42 g |
| Calcium chloride | 0.24 g |

The sensitive on the physiograph was adjusted according to the heart beat. The auricles were fixed in a pair of stimulating electrodes and kept vertically immersed inside the bath. The auricles were allowed to equilibrate for a period of 30 minutes. The electrode was connected to a stimulator (Medicare Research Stimulator SS44) at a duration of 5×1 misec and 5×0.1 misec delay kept constant. Initially the voltage and frequency were at a minimum. Then, the voltage was gradually increased until there was a change in amplitude. The frequency was then increased/adjusted to get arrhythmias. Doses of extract/fraction were given as concentrations of the salt per ml of bath solution and allowed to remain in contact with the auricles for 10 minutes. After every alternate minute, the physiograph was run to see if there was any change in heart rate. After 10 minutes, the auricles were stimulated twice for arrhythmias. The anti-arrhythmic effect of each dose, i.e., 3 and 10 µg/ml, was calculated. The formula used for evaluating the arrhythmic effect of the crude extract of *Salvadora persica* on guinea pig atrium was:

$$\% \text{ inhibition} = \frac{(X) - (Y) \times 100}{(X)}$$

wherein X=Maximum frequency before the extract.

Y=Maximum frequency after the extract.

The relative in vitro effect of *Salvadora persica* on a guinea pig atrium is

TABLE I

| EXTRACT | TISSUE | FREQUENCY BEFORE DRUG | FREQUENCY AFTER DRUG | PERCENTAGE CHANGE |
| --- | --- | --- | --- | --- |
| Crude Extract | Atrium | 96 beats/sec. | 96 beats/sec. | 0 |

The invention of this application has been described both generically and with regard to specific embodiments. Although the invention is set forth in what is believed to be the preferred embodiments, a wide variety of alternatives known to those of skill in the art can be selected within the generic disclosure. The invention is not otherwise limited, except for the recitation of the claims set forth below.

What is claimed is:

1. A method of treating cholinergic, arrhythmic and spasmodic conditions in a mammal comprising administering an effective amount of a chloroform fraction of an aqueous methanolic extract obtained from the mangrove plant *Salvadora persica*.

2. The method of claim 1, wherein said effective amount of chloroform fraction per dose is an amount from 3 $\mu$g/ml to 250 $\mu$g/ml.

3. The method of claim 2, wherein said effective amount of chloroform fraction per dose is from 50 $\mu$g/ml to 250 $\mu$g/ml.

4. The method of claim 2, wherein said effective amount of chloroform fraction per dose is from 3 $\mu$g/ml to 10 $\mu$g/ml.

5. The method of claim 1, wherein said mammal is a human.

6. The method of claim 1, wherein said spasmotic condition is a muscular spasm.

7. The method of claim 1, wherein said chloroform fraction is administered to said mammal for a period of 10 minutes.

8. The method of claim 1, wherein said cholinergic condition is bronchial asthma.

* * * * *